US009574181B2

(12) United States Patent
Trusheim et al.

(10) Patent No.: US 9,574,181 B2
(45) Date of Patent: *Feb. 21, 2017

(54) INFLUENZA VIRUS REASSORTMENT METHOD

(71) Applicant: Seqirus UK Limited, Berkshire (GB)

(72) Inventors: Heidi Trusheim, Apex, NC (US); Peter Mason, New York, NY (US); Michael Franti, Redding, CT (US); Björn Keiner, Basel (CH); Melissa Sackal, Watertown, MA (US); Juerg Hunziker, Aarau (CH); David Morrissey, Winchester, MA (US); François Jean-Charles Natt, Hesingue (CH)

(73) Assignee: Seqirus UK Limited, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/522,747

(22) Filed: Oct. 24, 2014

(65) Prior Publication Data
US 2015/0118746 A1 Apr. 30, 2015

Related U.S. Application Data

(63) Continuation of application No. 13/699,301, filed as application No. PCT/IB2011/052218 on May 20, 2011, now Pat. No. 8,945,904.

(60) Provisional application No. 61/396,110, filed on May 21, 2010.

(51) Int. Cl.
C12N 7/00 (2006.01)
A61K 39/12 (2006.01)
A61K 39/145 (2006.01)
C12N 15/113 (2010.01)
A61K 39/00 (2006.01)

(52) U.S. Cl.
CPC .............. C12N 7/00 (2013.01); A61K 39/12 (2013.01); A61K 39/145 (2013.01); C12N 15/1131 (2013.01); A61K 2039/525 (2013.01); C12N 2310/14 (2013.01); C12N 2320/00 (2013.01); C12N 2760/16134 (2013.01); C12N 2760/16151 (2013.01); C12N 2760/16152 (2013.01)

(58) Field of Classification Search
None
See application file for complete search history.

(56) References Cited

U.S. PATENT DOCUMENTS

| 5,948,410 | A | 9/1999 | Van Scharrenburg et al. |
| 6,080,725 | A | 6/2000 | Marciani |
| 8,945,904 | B2* | 2/2015 | Trusheim et al. ............ 435/239 |
| 2007/0014805 | A1 | 1/2007 | Dalencon et al. |
| 2007/0191314 | A1 | 8/2007 | Klucker et al. |

FOREIGN PATENT DOCUMENTS

| EP | 0870508 | 10/1998 |
| EP | 1174514 | 1/2002 |
| EP | 1260581 | 11/2002 |
| WO | WO-90/14837 | 12/1990 |
| WO | WO-95/11700 | 5/1995 |
| WO | WO-96/15231 | 5/1996 |
| WO | WO-97/37000 | 10/1997 |
| WO | WO-97/37001 | 10/1997 |
| WO | WO-01/21151 | 3/2001 |
| WO | WO-01/85938 | 11/2001 |
| WO | WO-02/28422 | 4/2002 |
| WO | WO-02/067983 | 9/2002 |
| WO | WO-02/074336 | 9/2002 |
| WO | WO-02/097072 | 12/2002 |
| WO | WO-03/023021 | 3/2003 |
| WO | WO-03/023025 | 3/2003 |
| WO | WO-03/043415 | 5/2003 |
| WO | WO-03/076601 | 9/2003 |
| WO | WO-2005/042728 | 5/2005 |
| WO | WO-2005/097181 | 10/2005 |
| WO | WO-2005/113756 | 12/2005 |
| WO | WO-2005/113758 | 12/2005 |
| WO | WO-2006/027698 | 3/2006 |
| WO | WO-2006/071563 | 7/2006 |
| WO | WO-2006/108846 | 10/2006 |
| WO | WO-2006/113373 | 10/2006 |
| WO | WO-2007/052061 | 5/2007 |
| WO | WO-2007/052163 | 5/2007 |
| WO | WO-2007/118284 | 10/2007 |
| WO | WO-2008/043774 | 4/2008 |
| WO | WO-2008/068631 | 6/2008 |
| WO | WO-2009/030440 | 3/2009 |

OTHER PUBLICATIONS

Mautino et al (Human Gene Therapy 11:2025-2037, 2000.*
Kwok et al. (2009). "Inhibition of influenza A virus replication by short double-stranded oligodeoxynucleotides," Archives of Virology 154(1):109-114.
Raza et al. (2011). "Selection of predicted siRNA as potential antiviral therapeutic agent against influenza virus," Bioinformation 6(9): 340-343.
International Search Report dated Sep. 15, 2011, for PCT/IB2011/052218 filed May 20, 2011, 4 pages.
International Preliminary Report of Patentability completed Oct. 9, 2012, for PCT/IB2011/052218 filed May 20, 2011, 7 pages.
Written Opinion of The International Searching Authority dated Nov. 21, 2012, for PCT/IB2011/052218 filed May 20, 2011, 5 pages.
Allison et al. (1992). "Syntex adjuvant formulation," Res Immunol 143(5):519-25.
Banzhoff et al. (2000). "Preservative-free influenza vaccine," Immunol Lett 71(2):91-6.
Brands et al. (1999). "Influvac: a safe Madin Darby Canine Kidney (MDCK) cell culture-based influenza vaccine," Dev Biol Stand. 98:93-100.

(Continued)

Primary Examiner — Benjamin P Blumel
(74) Attorney, Agent, or Firm — Finnegan, Henderson, Farabow, Garrett & Dunner, LLP

(57) ABSTRACT

Methods for producing reassortant viruses are provided wherein the transcription and/or translation of the hemagglutinin and/or neuraminidase genes are suppressed.

10 Claims, 1 Drawing Sheet

(56) References Cited

OTHER PUBLICATIONS

Brühl et al. (2000). "Humoral and cell-mediated immunity to vero cell-derived influenza vaccine," Vaccine 19(9-10):1149-58.
Chen et al. (2003). "Epidermal powder immunization of mice and monkeys with an influenza vaccine," Vaccine 21(21-22):2830-6.
Ge et al. (2003). "RNA interference of influenza virus production by directly targeting mRNA for degradation and indirectly inhibiting all viral RNA transcription," PNAS 100(5):2718-2723.
Greenbaum et al. (2004). "Mucosal (SIgA) and serum (IgG) immunologic responses in young adults following intranasal administration of one or two doses of inactivated, trivalent anti-influenza vaccine," Vaccine 22(20):2566-77.
Halperin et al. (1979). "A comparison of the intradermal and subcutaneous routes of influenza vaccination with A/New Jersey/76 (swine flu) and A/Victoria/75: report of a study and review of the literature," American Journal of Public Health 69(12):1247-1251.
Halperin et al. (2002). "Safety and immunogenicity of a trivalent, inactivated, mammalian cell culture-derived influenza vaccine in healthy adults, seniors, and children," Vaccine 20(7-8):1240-7.
Hariharan et al. (1995). "The induction of cytotoxic T cells and tumor regression by soluble antigen formulation," Cancer Res. 55(16):3486-9.
Herbert et al. (1979). "Comparison of responses to influenza A/New Jersey/76-A/Victoria/75 virus vaccine administered intradermally or subcutaneously to adults with chronic respiratory disease," J Infect Dis. 140(2):234-8.
Herlocher et al. (2004). "Influenza viruses resistant to the antiviral drug oseltamivir: transmission studies in ferrets," J Infect Dis. 190(9):1627-30.
Huckriede et al. (2003). "Influenza virosomes in vaccine development," Methods Enzymol. 373:74-91.
Keitel et al. (1996). "Increasing doses of purified influenza virus hemagglutinin and subvirion vaccines enhance antibody responses in the elderly," Clin Diagn Lab Immunol. 3(5): 507-510.
Kistner et al. (1998). "Development of a mammalian cell (Vero) derived candidate influenza virus vaccine," Vaccine 16(9-10):960-8.
Kistner et al. (1999). "Development of a Vero cell-derived influenza whole virus vaccine," Dev Biol Stand 98:101-10.
Klee et al. (2005). "AMOD: a morpholino oligonucleotide selection tool," Nucleic Acids Res. 33(Web Server issue):W506-11.
Le et al. (2005). "Avian flu: isolation of drug-resistant H5N1 virus," Nature 437(7062):1108.
Mann et al. (2004). "Optimisation of a lipid based oral delivery system containing A/Panama influenza haemagglutinin," Vaccine 22(19):2425-9.
Miller et al. (2003). "Allele-specific silencing of dominant disease genes," PNAS 100(12):7195-7200.
Nony et al. (2001). "Impact of osmolality on burning sensations during and immediately after intramuscular injection of 0.5 ml of vaccine suspensions in healthy adults," Vaccine. 19(27):3645-51.
Pau et al. (2001). "The human cell line PER.C6 provides a new manufacturing system for the production of influenza vaccines," Vaccine 19(17-19):2716-21.
Piascik (2003). "Intranasal flu vaccine available this season," J Am Pharm Assoc 43(6):728-30.
Podda et al. (2003). "MF59-adjuvanted vaccines: increased immunogenicity with an optimal safety profile," Expert Rev Vaccines (2):197-203.
Podda (2001). "The adjuvanted influenza vaccines with novel adjuvants: experience with the MF59-adjuvanted vaccine," Vaccine 19(17-19):2673-80.
Potter et al. (1979). "Determinants of immunity to influenza infection in man," Br Med Bull 35(1):69-75.
Rota et al. (1992). "Antigenic and genetic characterization of the haemagglutinins of recent cocirculating strains of influenza B virus," J Gen Virol 73( Pt 10):2737-42.
Smith & Waterman (1981). "Comparison of biosequences," Advances in Applied Mathematics 2(4):482-489.
Süli et al. (2004). "Experimental squalene adjuvant. I. Preparation and testing of its effectiveness," Vaccine 22(25-26):3464-9.
Summerton et al. (1997). "Morpholino antisense oligomers: design, preparation, and properties," Antisense Nucleic Acid Drug Dev 7(3):187-95.
Treanor et al. (1996). "Evaluation of a recombinant hemagglutinin expressed in insect cells as an influenza vaccine in young and elderly adults," J Infect Dis 173(6):1467-70.
Tree et al. (2001). "Comparison of large-scale mammalian cell culture systems with egg culture for the production of influenza virus A vaccine strains," Vaccine. 19(25-26):3444-50.
Zurbriggen et al. (2003). "Nonclinical safety evaluation of *Escherichia coli* heat-labile toxin mucosal adjuvant as a component of a nasal influenza vaccine," Expert Rev Vaccines. (2):295-304.

* cited by examiner

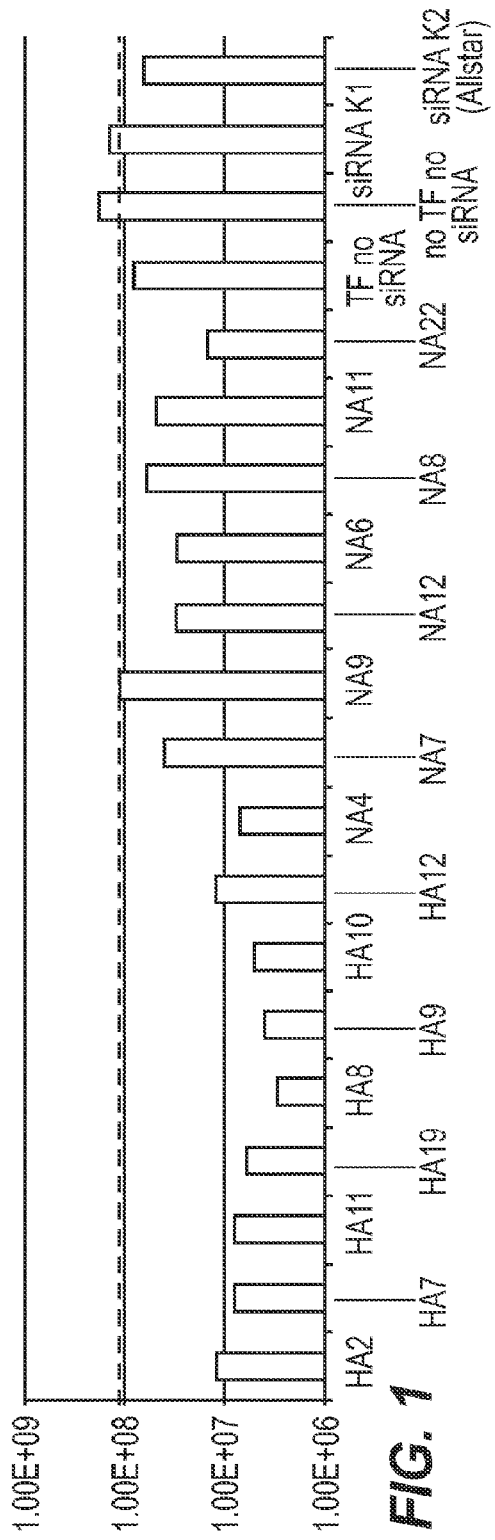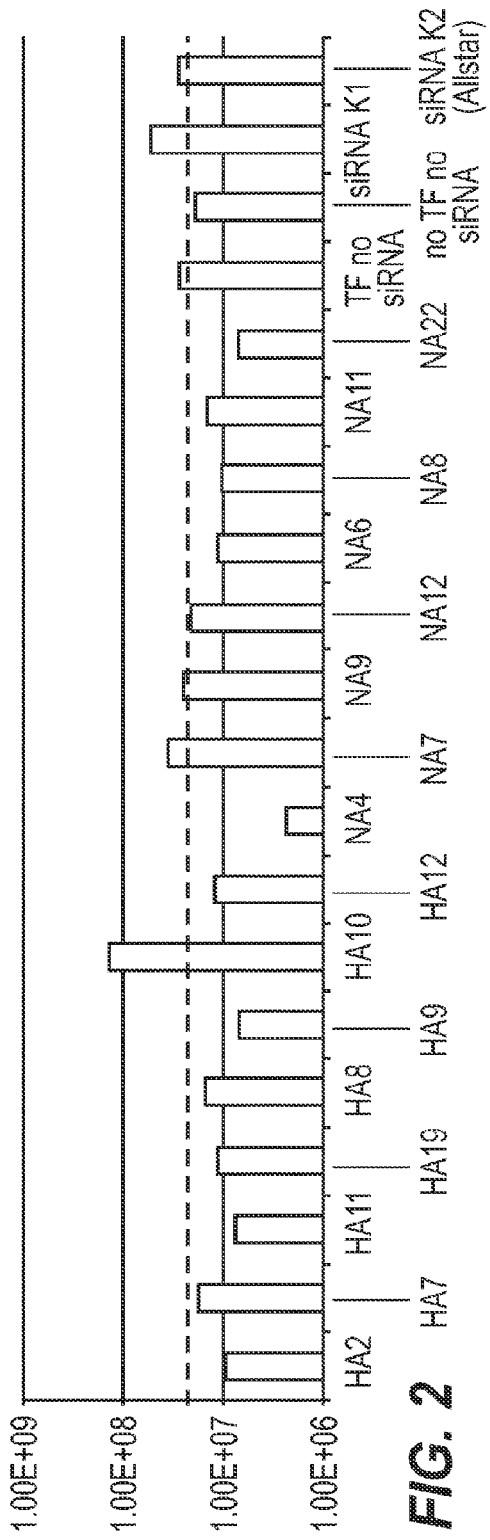

SEQUENCE LISTING

<160> NUMBER OF SEQ ID NOS: 130

<210> SEQ ID NO 1
<211> LENGTH: 1712
<212> TYPE: DNA
<213> ORGANISM: Influenza A virus (HA, A/Puerto Rico/8/34)

<400> SEQUENCE: 1

```
ggcaaaccta ctggtcctgt tatgtgcact tgcagctgca gatgcagaca caatatgtat      60
aggctaccat acgaacaatt caaccgacac tgttgacaca gtactcgaga agaatgtgac     120
agtgacacac tctgttaacc tgctcgaaga cagccacaac ggaaaactat gtagattaaa     180
aggaatagcc ccactacaat ggggaaatg taacatcgcc ggatggctct tgggaaaccc     240
agaatgcgac ccactgcttc cagtgagatc atggtcctac attgtagaaa caccaaactc     300
tgaaaatgga atatgttatc caggagattt catcgactat gaggagctga gggagcaatt     360
gagctcagtg tcatcattcg aaagattcga aatatttccc aaagaaagct catggcccaa     420
ccacaacaca aacggagtaa cggcagcatg ctcccatgag gggaaaagca gttttttacag     480 aaatttgcta tggctgacgg agaaggaggg ctcatacccca agctgaaaa attcttatgt     540 gaacaaaaaa gggaaagaag tccttgtact gtggggtatt catcacccgc taacagtaa     600 ggaacaacag aatctctatc agaatgaaaa tgcttatgtc tctgtagtga cttcaaatta     660
taacaggaga tttaccccgg aaatagcaga aagacccaaa gtaagagatc aagctgggag     720
gatgaactat tactggacct tgctaaaacc cggagacaca ataatatttg aggcaaatgg     780
aaatctaata gcaccaatgt atgctttcgc actgagtaga ggctttgggt ccggcatcat     840
cacctcaaac gcatcaatgc atgagtgtaa cacgaagtgt caaacacccc tgggagctat     900
aaacagcagt ctcccttacc agaatataca cccagtcaca ataggagagt gcccaaaata     960
cgtcaggagt gccaaattga ggatggttac aggactaagg aacattccgt ccattcaatc    1020
cagaggtcta tttggagcca ttgccggttt tattgaaggg ggatggactg gaatgataga    1080
tggatggtat ggttatcatc atcagaatga acagggatca ggctatgcag cggatcaaaa    1140
aagcacacaa aatgccatta acgggattac aaacaaggtg aacactgtta tcgagaaaat    1200
gaacattcaa ttcacagctg tgggtaaaga attcaacaaa ttagaaaaaa ggatggaaaa    1260
tttaaataaa aagttgatg atggatttct ggacatttgg acatataatg cagaattgtt    1320
agttctactg gaaaatgaaa ggactctgga attccatgac tcaaatgtga agaatctgta    1380
```

```
tgagaaagta aaaagccaat taaagaataa tgccaaagaa atcggaaatg gatgttttga   1440
gttctaccac aagtgtgaca atgaatgcat ggaaagtgta agaaatggga cttatgatta   1500
tcccaaatat tcagaagagt caaagttgaa cagggaaaag gtagatggag tgaaattgga   1560
atcaatgggg atctatcaga ttctggcgat ctactcaact gtcgccagtt cactggtgct   1620
tttggtctcc ctgggggcaa tcagtttctg gatgtgttct aatggatctt tgcagtgcag   1680
aatatgcatc tgagattaga atttcagaga ta                                  1712

<210> SEQ ID NO 2
<211> LENGTH: 1395
<212> TYPE: DNA
<213> ORGANISM: Influenza A virus (NA, A/Puerto Rico/8/34)

<400> SEQUENCE: 2
aaaagcaggg gtttaaaatg aatccaaatc agaaaataat aaccattgga tcaatctgtc     60
tggtagtcgg actaattagc ctaatattgc aaatagggaa tataatctca atatggatta    120
gccattcaat tcaaactgga agtcaaaacc atactggaat atgcaaccaa aacatcatta    180
cctataaaaa tagcacctgg gtaaaggaca caacttcagt gatattaacc ggcaattcat    240
ctctttgtcc catccgtggg tggctatat acagcaaaga caatagcata agaattggtt    300
ccaaaggaga cgtttttgtc ataagagagc cctttatttc atgttctcac ttggaatgca    360
ggaccttttt tctgacccaa ggtgccttac tgaatgacaa gcattcaagt gggactgtta    420
aggacagaag cccttatagg gccttaatga gctgccctgt cggtgaagct ccgtccccgt    480
acaattcaag atttgaatcg gttgcttggt cagcaagtgc atgtcatgat ggcatgggct    540
ggctaacaat cggaatttca ggtccagata atggagcagt ggctgtatta aaatacaacg    600
gcataataac tgaaaccata aaaagttgga ggaagaaaat attgaggaca caagagtctg    660
aatgtgcctg tgtaaatggt tcatgtttta ctataatgac tgatggcccg agtgatgggc    720
tggcctcgta caaaattttc aagatcgaaa aggggaaggt tactaaatca atagagttga    780
atgcacctaa ttctcactat gaggaatgtt cctgttaccc tgataccggc aaagtgatgt    840
gtgtgtgccg agacaattgg catggttcga accggccatg ggtgtctttc gatcaaaacc    900
tggattatca aataggatac atctgcagtg ggttttcgg tgacaacccg cgtcccgaag    960
atggaacagg cagctgtggt ccagtgtatg ttgatggagc aaacggagta aagggatttt   1020
catataggta tggtaatggt gtttggatag gaaggaccaa aagtcacagt tccagacatg   1080
ggtttgagat gatttgggat cctaatggat ggacagagac tgatagtaag ttctctgtga   1140
ggcaagatgt tgtggcaatg actgattggt cagggtatag cggaagtttc gttcaacatc   1200
ctgagctgac agggctagac tgtatgaggc cgtgcttctg ggttgaatta atcaggggac   1260
gacctaaaga aaaaacaatc tggactagtg cgagcagcat ttctttttgt ggcgtgaata   1320
gtgatactgt agattggtct tggccagacg gtgctgagtt gccattcagc attgacaagt   1380
agtctgttca aaaaa                                                     1395

<210> SEQ ID NO 3
<211> LENGTH: 1017
<212> TYPE: DNA
<213> ORGANISM: Influenza A virus (HA, A/Ann Arbor/6/60)

<400> SEQUENCE: 3
atggccatca tttatctcat tctcctgttc acagcagtga gaggggacca gatatgcatt     60
ggataccatg ccaataattc cacagagacg gtcgacacaa ttctagagcg gaacgtcact    120
```

```
gtgactcatg ccaaggacat tcttgagaag acccataacg aaagttatg caaactaaac      180 ggaatccctc cacttgaact aggggactgt agcattgccg gatggctcct ggaaatccca      240
gaatgtgata ggcttctaag tgtgccagaa tggtcctata taatggagaa agaaaacccg      300
agaaacggtt tgtgttatcc aggcaacttc aatgattatg aagaattgaa acatctcctc      360
agcagcgtga acatttcga gaaagtaaag attctgccca agatagatg gacacagcat       420 acaacaactg gaggttcaca ggcctgcgcg tgtctggta atccatcatt cttcaggaac       480
atggtctggc tgacagagaa agaatcaaat tatccggttg ccaaggatc gtacaacaat       540 acaagcggaa acaaatgct aataatttgg ggggtgcacc atcccattga tgagaaagaa      600
caaagaacat tgtaccagaa tgtgggaacc tatgtttccg taggcacatc aacattgaac      660
aaaaggtcaa ccccagaaat agcaacaagg cctaaagtga atggactagg aagtagaatg      720
gaattctctt ggaccctctt ggatatgtgg gacaccataa cttttgagag tactggtaat      780
ctaattgcac cagagtatgg attcaaaata tcgaaaagag tagttctgg gatcatgaaa      840 acagaaggaa cacttgagaa ctgtgagacc aaatgccaaa ctccttgggg agcaataaat      900
acaacattgc cttttcacaa tgtccaccca ctgacaatag gtgagtgccc caaatatgta      960
aaatcggaga agttggtctt agcaacagga ctaaggaatg ttccccagat tgaatca      1017
```

<210> SEQ ID NO 4
<211> LENGTH: 1410
<212> TYPE: DNA
<213> ORGANISM: Influenza A virus (NA, A/Ann Arbor/6/60)

<400> SEQUENCE: 4

```
atgaatccaa atcaaaagat aataacaatt ggctctgtct ctctcaccat tgcaacagta      60
tgcttcctca tgcagattgc catcctggca actactgtga cattgcattt taagcaacat      120
gagtgcgact cccccgcgag caaccaagta atgccatgtg aaccaataat aatagaaagg      180
aacataacag agatagtgta tttgaataac accaccatag agaaagagat tgccccgaa       240 gtagtggaat acagaaattg gtcaaagccg caatgtcaaa ttacaggatt tgcaccttt       300 tctaaggaca attcaatccg gctttctgct ggtgggggaca tttgggtgac gagagaacct     360
tatgtgtcat gcgatcctgg caagtgttat caatttgcac tcgggcaggg gaccacacta     420
gacaacaaac attcaaatgg cacaatacat gatagaagcc ctcatcgaac cctattaatg     480
aatgagttgg gtgttccatt tcatttagga accaaacaag tgtgtgcagc atggtccagc     540
tcaagttgtc acgatggaaa agcatggttg catgtttgtg tcactgggga tgatagaaat     600
gcaactgcta gcttcattta tgacgggagg cttgtggaca gtattggttc atggtctcaa     660
aatatcctca ggacccagga gtcggaatgc gtttgtatca atgggacttg cacagtagta     720
atgactgatg gaagtgcatc aggaagagcc gatactagaa tactattcat taaagaggg      780 aaaattgtcc atattggccc attgtcagga agtgctcagc atatagagga gtgttcttgt     840 tacccctcgat atcctgacgt cagatgtatc tgcagagaca actggaaagg ctctaatagg    900
cccgttatag acataaatat ggaagattat agcattgatt ccagttatgt gtgctcaggg     960
cttgttggcg acacacccag gaacgacgac agctctagca atagcaattg cagggatcct    1020
aacaatgaaa gagggaatcc aggagtgaaa ggctgggcct tgacaatgg agatgatgta     1080 tggatgggaa gacaatcag caaagattta cgctcaggtt atgaacttt caagtcatt      1140 ggtggttggt ccacacctaa ttccaaatcg caggtcaata gacaggtcat agttgacaac     1200
```

| | |
|---|---|
| aataattggt ctggttactc tggtattttc tctgttgagg gcaaaagctg catcaatagg | 1260 |
| tgcttttatg tggagttgat aaggggaagg ccacaggaga ctagagtatg gtggacctca | 1320 |
| aacagtattg ttgtattttg tggcacttca ggtacttatg gaacaggctc atggcctgat | 1380 |
| ggggcgaaca tcaatttcat gcctatataa | 1410 |

<210> SEQ ID NO 5
<211> LENGTH: 1773
<212> TYPE: RNA
<213> ORGANISM: Influenza A virus (HA complete sequence, A/Ann
      Arbor/6/60)

<400> SEQUENCE: 5

| | |
|---|---|
| agcaaaagca ggguuauac cauagacaac caaaagcaaa acaauggcca ucauuuaucu | 60 |
| cauucuccug uucacagcag ugagagggga caagauaugc auuggauacc augccaauaa | 120 |
| uuccacagag acggucgaca caauucuaga gcggaacguc acugugacuc augccaagga | 180 |
| cauucuuag aagacccaua acggaaaguu augcaaacua acggaauccc cuccacuuga | 240 |
| acuaggggac uguagcauug ccggauggcu ccuuggaaau ccagaaugug auaggcuucu | 300 |
| aagugugcca aauggucccu auauaaugga gaaagaaaac ccgagaaacg guuuguguua | 360 |
| uccaggcaac uucaaugauu augaagaauu gaaacaucuc cucagcagcg ugaaacauuu | 420 |
| cgagaaagua aagauucugc ccaaagauag auggacacag cauacaacaa cuggagguuc | 480 |
| acaggccugc gcggugucug uaauccauc auucuucagg aacaugguucu ggcugacaga | 540 |
| ggaaggauca aauuauccgg uugccaaagg aucuacaac aauacaagcg agaacaaau | 600 |
| gcuaauaauu ggggggugc accaucccau ugaugagaca gaacaaagaa cauuguacca | 660 |
| gaaugggga accauguuu ccguaggcac aucaacauug aacaaaaggu caaccccaga | 720 |
| aauagcaaca aggccuaaag ugaauggacu aggaaguaga auggaauucu cuggacccu | 780 |
| cuuggauaug uggacacca uaaauuuuga gaguacuggu aaucuaauug caccagagua | 840 |
| uggauucaaa auaucgaaaa gagguaguuc ugggaucaug aaaacagaag gaacacuuga | 900 |
| gaacugugag accaaaugcc aaacuccuuu gggagcaaua aauacaacau gccuuuuuca | 960 |
| caaugucccac ccacugacaa uaggugagug cccccaaauau guaaaaucgg agaaguuggu | 1020 |
| cuuagcaaca ggacuaagga auguucccca gauugaauca agaggauugu uuggggcaau | 1080 |
| agcuggguuuu auagaaggag gauggcaagg aaugguugau gguuguaug gauaccauca | 1140 |
| cagcaaugac cagggaucag gguaugcagc agacaaagaa uccacucaaa aggcauuuga | 1200 |
| uggaaucacc aacaagguaa auucugugau ugaaaagaua aacacccau uugaagcugu | 1260 |
| ugggaaagaa uucaguaacu uagagagaag acuggagaac uugaacaaaa gauggaaga | 1320 |
| cggguuucua gauguguga cauacaaugc ugagcuucua guucgaugg aaaaugagag | 1380 |
| gacacuugac uuucaugauu cuaaugucaa gaaucuguau gauaaaguca gaaugcagcu | 1440 |
| gagggacaac gucaaagaac uaggaaaugg auguuugaa uuuuaucaca aaugugauga | 1500 |
| ugaaugcaug aauagugugaa aaacggggac auaugauuau cccaaguaug aagaagaguc | 1560 |
| uaaacuaaau agaaaugaa uuaaaggggu aaaauugagc agcauggggg uuugucggau | 1620 |
| ccuugccauu uaugcuacag uagcagguuc ucugucacug gcaaucauga uggcuggau | 1680 |
| cucuuucugg augcucca acgggucucu gcagugcagg aucugcauau gauuauaagu | 1740 |
| cauuuuauaa uuaaaaacac ccuuguuucu acu | 1773 |

<210> SEQ ID NO 6

<211> LENGTH: 1467
<212> TYPE: RNA
<213> ORGANISM: Influenza A virus (NA complete sequence, A/Ann Arbor/6/60)

<400> SEQUENCE: 6

```
agcaaaagca ggagugaaaa ugaauccaaa ucaaaagaca aua

```
Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495
```

```
Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 566
<212> TYPE: PRT
<213> ORGANISM: Influenza A virus (HA, A/Chile/1/1983)

<400> SEQUENCE: 8

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300
```

```
Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 9
<211> LENGTH: 469
<212> TYPE: PRT
<213> ORGANISM: Influenza A virus (NA, A/California/04/09)

<400> SEQUENCE: 9

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
                20                  25                  30

Trp Ile Ser His Ser Ile Gln Leu Gly Asn Gln Asn Gln Ile Glu Thr
            35                  40                  45

Cys Asn Gln Ser Val Ile Thr Tyr Glu Asn Asn Thr Trp Val Asn Gln
        50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
```

```
                    100                 105                 110
Asp Val Phe Val Ile Arg Glu Pro Phe Ile Ser Cys Ser Pro Leu Glu
            115                 120                 125
Cys Arg Thr Phe Phe Leu Thr Gln Gly Ala Leu Leu Asn Asp Lys His
        130                 135                 140
Ser Asn Gly Thr Ile Lys Asp Arg Ser Pro Tyr Arg Thr Leu Met Ser
145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
            180                 185                 190
Ile Gly Ile Ser Gly Pro Asp Asn Gly Ala Val Ala Val Leu Lys Tyr
        195                 200                 205
Asn Gly Ile Ile Thr Asp Thr Ile Lys Ser Trp Arg Asn Asn Ile Leu
    210                 215                 220
Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Ile Val Lys Ser Val Glu Met Asn Ala Pro
            260                 265                 270
Asn Tyr His Tyr Glu Glu Cys Ser Cys Tyr Pro Asp Ser Ser Glu Ile
        275                 280                 285
Thr Cys Val Cys Arg Asp Asn Trp His Gly Ser Asn Arg Pro Trp Val
    290                 295                 300
Ser Phe Asn Gln Asn Leu Glu Tyr Gln Ile Gly Tyr Ile Cys Ser Gly
305                 310                 315                 320
Ile Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
            340                 345                 350
Tyr Gly Asn Gly Val Trp Ile Gly Arg Thr Lys Ser Ile Ser Ser Arg
        355                 360                 365
Asn Gly Phe Glu Met Ile Trp Asp Pro Asn Gly Trp Thr Gly Thr Asp
    370                 375                 380
Asn Asn Phe Ser Ile Lys Gln Asp Ile Val Gly Ile Asn Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
            420                 425                 430
Glu Asn Thr Ile Trp Thr Ser Gly Ser Ser Ile Ser Phe Cys Gly Val
        435                 440                 445
Asn Ser Asp Thr Val Gly Trp Ser Trp Pro Asp Gly Ala Glu Leu Pro
    450                 455                 460
Phe Thr Ile Asp Lys
465

<210> SEQ ID NO 10
<211> LENGTH: 470
<212> TYPE: PRT
<213> ORGANISM: Influenza A viurs (NA, A/Chile/1/1983)

<400> SEQUENCE: 10
```

-continued

```
Met Asn Pro Asn Gln Lys Ile Ile Thr Ile Gly Ser Ile Cys Met Thr
1               5                   10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
50                  55                  60

Thr Tyr Val Asn Ile Asn Asn Thr Asn Val Val Ala Gly Lys Asp Thr
65                  70                  75                  80

Thr Ser Val Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Arg Ile Leu
210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
```

```
                420             425             430
Glu Gly Thr Thr Val Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
    450                 455                 460

Pro Phe Thr Ile Asp Lys
465                 470
```

<210> SEQ ID NO 11
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 11
ugggccucug uguuauuau                                              19

<210> SEQ ID NO 12
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 12
ugagacucuu accuuauac                                              19

<210> SEQ ID NO 13
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 13
gggccucugu guuauuaua                                              19

<210> SEQ ID NO 14
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 14
gacccuccua cuugauaau                                              19

<210> SEQ ID NO 15
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 15
gggccuuuau cgucuuucu                                              19

<210> SEQ ID NO 16
<211> LENGTH: 19
<212> TYPE: RNA
<213> ORGANISM: Artificial Sequence
<220> FEATURE:
<223> OTHER INFORMATION: Antisense strand of siRNA

```
<400> SEQUENCE: 16
ccguuuaccu uuagauuau                                                19

<210> SEQ ID NO 17
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 17
cagagggaaa ggucuuaua                                                19

<210> SEQ ID NO 18
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 18
cccuccuacu ugauaauga                                                19

<210> SEQ ID NO 19
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 19
caggauguaa caucuuugu                                                19

<210> SEQ ID NO 20
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 20 cugguuuca uucucuagu                                                 19

<210> SEQ ID NO 21
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 21
ccugauuaau cggauuaua                                                19

<210> SEQ ID NO 22
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 22
cccgauauau gucguuucu                                                19

<210> SEQ ID NO 23
<211> LENGTH: 19
```

```
<212> TYPE: RNA
<213> ORGANISM: Artificial Sequence
<220> FEATURE:
<223> OTHER INFORMATION: Antisense strand of siRNA

<400> SEQUENCE: 23
cgaagaccca acuuaauua                                                19

<210> SEQ ID NO 24
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 24
gccugauuaa ucggauuau                                                19

<210> SEQ ID NO 25
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 25
cggacacauu uaccaagua                                                19

<210> SEQ ID NO 26
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 26
cgggaaauaa aguacaaga                                                19

<210> SEQ ID NO 27
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 27
gccguuaagu agagaaaca                                                19

<210> SEQ ID NO 28
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 28
cgccuucaaa gcaaguugu                                                19

<210> SEQ ID NO 29
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 29
```
cagaccauca gccugauua                                              19

<210> SEQ ID NO 30
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 30
cccugacaau uccugucuu                                              19

<210> SEQ ID NO 31
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 31
cacccgauau augucguuu                                              19

<210> SEQ ID NO 32
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 32
guaaagcucu uucauuucu                                              19

<210> SEQ ID NO 33
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 33
cgccucuugu uuacgauua                                              19

<210> SEQ ID NO 34
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 34
ccucuuguuu acgauuauu                                              19

<210> SEQ ID NO 35
<211> LENGTH: 18
<212> TYPE: RNA
<213> ORGANISM: Artificial Sequence
<220> FEATURE:
<223> OTHER INFORMATION: Antisense strand of siRNA

<400> SEQUENCE: 35
cucguuauuu auguugua                                               18

<210> SEQ ID NO 36
<211> LENGTH: 19
<212> TYPE: RNA
<213> ORGANISM: Artificial Sequence

```
<220> FEATURE:
<223> OTHER INFORMATION: Antisense strand of siRNA

<400> SEQUENCE: 36
cacggucuua ccaggauau                                                        19

<210> SEQ ID NO 37
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 37
gccucuuguu uacgauuau                                                        19

<210> SEQ ID NO 38
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 38
guccguugaa guuacuaau                                                        19

<210> SEQ ID NO 39
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 39
cguggucuca uaccuaagu                                                        19

<210> SEQ ID NO 40
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 40
ggucuuacca ggauauauu                                                        19

<210> SEQ ID NO 41
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 41
ccgggcaaua ucuguauuu                                                        19

<210> SEQ ID NO 42
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 42
cgggcaauau cuguauuua                                                        19
```

<210> SEQ ID NO 43
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 43
cccacaaggu aaaguaaau                                              19

<210> SEQ ID NO 44
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 44
cccgcuugua guuaaagua                                              19

<210> SEQ ID NO 45
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 45
cggcguuaca guuuaaugu                                              19

<210> SEQ ID NO 46
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 46
gggaguagcu ugggauaau                                              19

<210> SEQ ID NO 47
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 47
cggcuaugau cuuaugaua                                              19

<210> SEQ ID NO 48
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 48
ccuggaguuu gucauaaca                                              19

<210> SEQ ID NO 49
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 49
gggccucugu guuauuaua                                                19

<210> SEQ ID NO 50
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 50
cgguacacuu gguuauuau                                                19

<210> SEQ ID NO 51
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 51
cuggucuuaa agucuuuau                                                19

<210> SEQ ID NO 52
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 52
ccguuuaccu uuagauuau                                                19

<210> SEQ ID NO 53
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 53
ggaccuguaa accuguaua                                                19

<210> SEQ ID NO 54
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 54
cccuguguua uuauaaacu                                                19

<210> SEQ ID NO 55
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 55
cuggguuuca uucuuuagu                                                19

<210> SEQ ID NO 56

<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 56
gaccuguaaa ccuguauau                                                      19

<210> SEQ ID NO 57
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 57
cuccuugacu cccuuguua                                                      19

<210> SEQ ID NO 58
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 58
cccauuucuu aaguuguuu                                                      19

<210> SEQ ID NO 59
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 59
ccagaaacgu cacgucuua                                                      19

<210> SEQ ID NO 60
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 60
caggauguaa cgucuuugu                                                      19

<210> SEQ ID NO 61
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 61
cugguuccac cgagauaau                                                      19

<210> SEQ ID NO 62
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 62
cccgauauau gucguuucu                                                19

<210> SEQ ID NO 63
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 63
cgaagaccca acuuaauua                                                19

<210> SEQ ID NO 64
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 64
gacccauuua guuuguaua                                                19

<210> SEQ ID NO 65
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 65
gccguuaagu agagaaaca                                                19

<210> SEQ ID NO 66
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 66
cgaggucuuu cccuaaacu                                                19

<210> SEQ ID NO 67
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 67
gguuccacga gauaauuua                                                19

<210> SEQ ID NO 68
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 68
cgccuucaaa gcaaguugu                                                19

<210> SEQ ID NO 69
<211> LENGTH: 19
<212> TYPE: RNA

```
<213> ORGANISM: Artificial Sequence
<220> FEATURE:
<223> OTHER INFORMATION: Antisense strand of siRNA

<400> SEQUENCE: 69
cccauuuagu uuguauaca                                                    19

<210> SEQ ID NO 70
<211> LENGTH: 19
<212> TYPE: RNA
<213> ORGANISM: Artificial Sequence
<220> FEATURE:
<223> OTHER INFORMATION: Antisense strand of siRNA

<400> SEQUENCE: 70
cggagcaugu cuuagaagu                                                    19

<210> SEQ ID NO 71
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 71
tttgggataa tcataagtc                                                    19

<210> SEQ ID NO 72
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 72
tttgttgaat tctttaccc                                                    19

<210> SEQ ID NO 73
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 73
ttctgcactg caaagatcc                                                    19

<210> SEQ ID NO 74
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 74
ttgattccaa tttcactcc                                                    19

<210> SEQ ID NO 75
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 75
ttctttggga aatatttcg                                                    19
```

<210> SEQ ID NO 76
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 76
taatctcaga tgcatattc                                                   19

<210> SEQ ID NO 77
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 77
ttcattctga tagagattc                                                   19

<210> SEQ ID NO 78
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 78
ttcaccttgt ttgtaatcc                                                   19

<210> SEQ ID NO 79
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 79
tttcttacac tttccatgc                                                   19

<210> SEQ ID NO 80
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 80
tagacctctg gattgaatg                                                   19

<210> SEQ ID NO 81
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 81
tactttctca tacagattc                                                   19

<210> SEQ ID NO 82
<211> LENGTH: 19
<212> TYPE: DNA
<213> ORGANISM: Artificial Sequence
<220> FEATURE:

<223> OTHER INFORMATION: Antisense strand of siRNA (shown in DNA format)

<400> SEQUENCE: 82
tacactcatg cattgatgc         19

<210> SEQ ID NO 83
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 83
tttggtgttt ctacaatgt         19

<210> SEQ ID NO 84
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 84
tcagctttgg gtatgagcc         19

<210> SEQ ID NO 85
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 85
tagtcctgta accatcctc         19

<210> SEQ ID NO 86
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 86
atttcttaca ctttccatg         19

<210> SEQ ID NO 87
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 87
tactgtgtca acagtgtcg         19

<210> SEQ ID NO 88
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 88
ttacactttc catgcattc         19

```
<210> SEQ ID NO 89
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 89
tttgtaatcc cgttaatgg                                               19

<210> SEQ ID NO 90
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 90
atagagattc tgttgttcc                                               19

<210> SEQ ID NO 91
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 91
ttgggataat cataagtcc                                               19

<210> SEQ ID NO 92
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 92
ttgaattctt tacccacag                                               19

<210> SEQ ID NO 93
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 93
tttgtgttgt ggttgggcc                                               19

<210> SEQ ID NO 94
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 94
ttcttctcga gtactgtgt                                               19

<210> SEQ ID NO 95
<211> LENGTH: 19
<212> TYPE: DNA
<213> ORGANISM: Artificial Sequence
<220> FEATURE:
<223> OTHER INFORMATION: Antisense strand of siRNA (shown in DNA format)
```

```
<400> SEQUENCE: 95
tacagtatca ctattcacg                                             19

<210> SEQ ID NO 96
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 96
tttaatacag ccactgctc                                             19

<210> SEQ ID NO 97
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 97
attgatttag taaccttcc                                             19

<210> SEQ ID NO 98
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 98
tatctggacc tgaaattcc                                             19

<210> SEQ ID NO 99
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 99
ttgatttagt aaccttccc                                             19

<210> SEQ ID NO 100
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 100
ttgaattgaa tggctaatc                                             19

<210> SEQ ID NO 101
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 101
ttgctgtata tagcccacc                                             19

<210> SEQ ID NO 102
<211> LENGTH: 19
```

<212> TYPE: DNA
<213> ORGANISM: Artificial Sequence
<220> FEATURE:
<223> OTHER INFORMATION: Antisense strand of siRNA (shown in DNA format)

<400> SEQUENCE: 102
ttgccggtta atatcactg                                                  19

<210> SEQ ID NO 103
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 103
taacagtccc acttgaatg                                                  19

<210> SEQ ID NO 104
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 104
tttggttgca tattccagt                                                  19

<210> SEQ ID NO 105
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 105
tattaggcta attagtccg                                                  19

<210> SEQ ID NO 106
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 106
tttggaacca attcttatg                                                  19

<210> SEQ ID NO 107
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 107
atctacagta tcactattc                                                  19

<210> SEQ ID NO 108
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 108
tacttgtcaa tgctgaatg                                                  19

<210> SEQ ID NO 109
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 109
ttactatcag tctctgtcc                                                  19

<210> SEQ ID NO 110
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 110
ttgacttcca gtttgaatt                                                  19

<210> SEQ ID NO 111
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 111
attaattcaa cccagaagc                                                  19

<210> SEQ ID NO 112
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 112
tcctatttga taatccagg                                                  19

<210> SEQ ID NO 113
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 113
tgaattgaat ggctaatcc                                                  19

<210> SEQ ID NO 114
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 114
ttccagtttg aattgaatg                                                  19

<210> SEQ ID NO 115
<211> LENGTH: 19
<212> TYPE: DNA
<213> ORGANISM: Artificial Sequence

```
<220> FEATURE:
<223> OTHER INFORMATION: Antisense strand of siRNA (shown in DNA format)

<400> SEQUENCE: 115
atggtttcag ttattatgc                                                    19

<210> SEQ ID NO 116
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 116
atgttgaacg aaacttccg                                                    19

<210> SEQ ID NO 117
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 117
attgccacaa catcttgcc                                                    19

<210> SEQ ID NO 118
<211> LENGTH: 19
<212> TYPE: DNA
<213> ORGANISM: Artificial Sequence
<220> FEATURE:
<223> OTHER INFORMATION: Antisense strand of siRNA (shown in DNA format)

<400> SEQUENCE: 118
ttggaaccaa ttcttatgc                                                    19

<210> SEQ ID NO 119
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 119
gggcctctgt gttattatag gggggtata ataacacaga ggccc                        45

<210> SEQ ID NO 120
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 120
tgggcctctg tgttattatg gggggataa taacacagag gccca                        45

<210> SEQ ID NO 121
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 121
gtaaagctct tcatttctg gggggagaa atgaaagagc tttac                         45
```

```
<210> SEQ ID NO 122
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 122
cgcctcttgt ttacgattag ggggggtaat cgtaaacaag aggcg              45

<210> SEQ ID NO 123
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 123
ctggtcttaa agtctttatg gggggataa agactttaag accag               45
```

Note: Reading carefully:

```
ctggtcttaa agtctttatg ggggggataa agactttaag accag              45

<210> SEQ ID NO 124
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 124
ccgtttacct ttagattatg ggggggataa tctaaaggta aacgg              45

<210> SEQ ID NO 125
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 125
cctgattaat cggattatag gggggtata atccgattaa tcagg               45
```

Corrected:

```
cctgattaat cggattatag ggggggtata atccgattaa tcagg              45

<210> SEQ ID NO 126
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 126
cccgatatat gtcgtttctg ggggggagaa acgacatata tcggg              45

<210> SEQ ID NO 127
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 127
ccgggcaata tctgtatttg ggggggaaat acagatattg cccgg              45

<210> SEQ ID NO 128
<211> LENGTH: 45
<212> TYPE: DNA
<213> ORGANISM: Artificial Sequence
<220> FEATURE:
<223> OTHER INFORMATION: shRNA (shown in DNA format)
```

```
<400> SEQUENCE: 128
cgggcaatat ctgtatttag gggggggtaaa tacagatatt gcccg                    45

<210> SEQ ID NO 129
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 129
ctgggttcca cgagataatg gggggggatta tctcgtggaa cccag                    45

<210> SEQ ID NO 130
<211> LENGTH: 45
<212> TYPE: DNA
<213> ORGANISM: Artificial Sequence
<220> FEATURE:
<223> OTHER INFORMATION: shRNA (shown in DNA format)

<400> SEQUENCE: 130
cccgatatat gtcgtttctg gggggggagaa acgacatata tcggg                    45
```

INFLUENZA VIRUS REASSORTMENT METHOD

CROSS REFERENCE TO RELATED APPLICATIONS

This application is a continuation of U.S. patent application Ser. No. 13/699,301, filed on Apr. 20, 2012, now allowed, which is a 35 U.S.C. 371 National Stage of International Application No. PCT/IB2011/052218, entitled "INFLUENZA VIRUS REASSORTMENT METHOD" filed May 20, 2011, which claims the benefit of and priority to U.S. Provisional patent application Ser. No. 61/396,110 filed May 21, 2010, all of which are hereby incorporated by reference in the present disclosure in their entirety.

SEQUENCE LISTING

The present application contains a Sequence Listing, which has been submitted in ASCII format via EFS-Web and is hereby incorporated by reference in its entirety. The ASCII copy, created on Dec. 23, 2014 is named PAT054189-US-CNT_SequenceListing.txt and is 54,744 bytes in size.

TECHNICAL FIELD

This invention is in the field of influenza virus reassortment. Furthermore, it relates to manufacturing vaccines for protecting against influenza viruses.

BACKGROUND ART

The most efficient protection against influenza infection is vaccination against the circulating strain and it is important to produce influenza viruses for vaccine production as quickly as possible.

Wild-type influenza virus typically grows very slowly in eggs and cell culture. In order to obtain a faster-growing virus strain for vaccine production it is currently common practice to reassort the circulating influenza strain (referred to herein as the vaccine strain) with a faster-growing high-yield backbone strain. This can be achieved by co-infecting cells in cell culture or the amniotic fluid of embryonated hen eggs with the vaccine strain and the backbone strain. Antibodies specific for the backbone strain's hemagglutinin (HA) and neuraminidase (NA) proteins are then added to block influenza viruses which carry the backbone strain's HA and/or NA protein from replicating. Over several passages of this treatment one can select for fast-growing reassortant influenza viruses which contain the HA and NA segments from the vaccine strain and the other viral segments (i.e. those encoding PB1, PB2, PA, NP, M1, M2, NS1 and NS2) from the backbone strain.

The current approaches have several drawbacks. For example, it typically takes about 35 days from the arrival of a new influenza strain to obtain the final high-growth reassortant, which causes delays in the production of influenza vaccines. Furthermore, the need to passage the viruses several times increases the risk for mutations in the HA antigen to occur which can result in an unwanted change of antigenicity. The use of polyclonal antisera to inhibit the propagation of non-reassorted viruses also increases the risk of introducing adventitious viral agents and other contaminants.

It is an object of the invention to provide further and improved methods for producing reassortant influenza viruses.

SUMMARY OF PREFERRED EMBODIMENTS

The inventors have now surprisingly discovered that preferentially reducing the transcription and/or translation of the backbone strain's HA and/or NA genes during virus production (e.g. by using RNA inhibition) can greatly increase the speed by which reassortant viruses are produced. The methods further have the advantage that they do not rely on the use of antibodies and so the use of animal derived products may be avoided. Furthermore, the likelihood of spontaneous mutations is lower as fewer passages are necessary to obtain reassortant viruses.

The invention provides a method for preparing a reassortant influenza virus comprising the steps of (i) infecting a culture host with a first influenza strain and a second influenza strain; (ii) contacting the culture host of step (i) with an inhibitory agent wherein said inhibitory agent preferentially reduces the transcription and/or translation of the hemagglutinin and/or neuraminidase genes of one of the influenza strains of (i); (iii) culturing the culture host in order to produce reassortant virus and optionally (iv) purifying the virus obtained in step (iii).

The methods of the invention may further comprise steps of (v) infecting a culture host with the reassortant virus obtained in step (iii) or step (iv); (vi) culturing the host from step (v) to produce further virus; and optionally (vii) purifying virus obtained in step (vi).

The invention provides a method of preparing a reassortant influenza virus comprising the steps of (i) infecting a culture host with a first influenza virus strain having at least one target segment; (ii) introducing into the culture host one or more expression construct(s) encoding the target segment(s) from a second influenza virus strain; (iii) contacting the culture host with an inhibitory agent which preferentially reduces the transcription and/or translation of the first influenza strain's target segment(s); (iv) culturing the culture host in order to produce reassortant virus; and optionally (v) purifying the virus obtained in step (iv).

The invention provides a cell comprising expression construct(s) encoding: (i) all eight viral segments of a first influenza A or B virus genome; (ii) at least one target segment of a second influenza A or B virus genome, wherein the second influenza strain's target segment(s) differs in sequence from the target segment of the first influenza strain; and (iii) an inhibitory agent wherein said inhibitory agent preferentially reduces transcription and/or translation of the target segment(s) in the first influenza strain.

The invention also provides a method for preparing a reassortant influenza virus comprising a step of culturing this cell in order to produce reassortant virus. The method may further comprise steps of infecting a culture host with the reassortant virus obtained from the cell, then culturing the host to produce further virus, and then (optionally) purifying the further virus obtained in this way.

The invention also provides a method for producing influenza viruses comprising the steps of (a) infecting a culture host with a reassortant virus obtained by the methods of the invention; (b) culturing the host from step (a) to produce the virus; and optionally (c) purifying the virus obtained in step (b).

The invention also provides a method of preparing a vaccine, comprising the steps of (d) preparing a virus by the methods of any one of the embodiments described above and (e) preparing vaccine from the virus.

Influenza Strains

Influenza viruses are segmented negative strand RNA viruses. Influenza A and B viruses have eight segments (PB2, PB1, PA, HA, NP, NA, M and NS), whereas influenza C virus has seven (no NA segment). The virus requires the presence of at least four viral proteins (PB1, PB2, PA and nucleoprotein) to initiate genome replication.

The methods of the invention use influenza backbone strain(s) and vaccine strain(s). The backbone strain and vaccine strain used will usually differ in one or more (e.g. 2, 3, 4, 5, 6, 7 or 8) viral segments that can be differentially inhibited by inhibitory agents as described below. The backbone strain is inhibited more than the vaccine strain for the desired segment(s) and therefore production of a reassortant strain is favoured.

The vaccine strains can be pandemic as well as interpandemic (seasonal) influenza strains. The vaccine strains may contain the influenza A virus HA subtypes H1, H2, H3, H4, H5, H6, H7, H8, H9, H10, H11, H12, H13, H14, H15 or H16. They may contain the influenza A virus NA subtypes N1, N2, N3, N4, N5, N6, N7, N8 or N9. Where the vaccine strain is a seasonal influenza strain, the vaccine strain may have a H1 or H3 subtype. In one aspect of the invention the vaccine strain is a H1N1 or H3N2 strain.

The vaccine strains may also be pandemic strains or potentially pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A vaccine strain with H5 hemagglutinin type is preferred where the reassortant virus is used in vaccines for immunizing against pandemic influenza, such as a H5N1 strain. Other possible strains include H5N3, H9N2, H2N2, H7N1 and H7N7, and any other emerging potentially pandemic strains. The invention is particularly suitable for producing reassortant viruses for use in vaccines for protecting against potential pandemic virus strains that can or have spread from a non-human animal population to humans, for example a swine-origin H1N1 influenza strain.

The backbone strain can be any known influenza virus strain but it is preferred that it is an influenza virus strain that grows quickly in cells and/or the allantoic fluid of eggs. This is preferred because reassortant influenza viruses are often produced in order to obtain a fast growing influenza virus for vaccine production. Examples of such backbone strains include but are not limited to A/Puerto Rico/8/34, A/Ann Arbor/6/60 and B/Ann Arbor/1/66.

A reassortant influenza A virus produced according to the invention may include one or more RNA segments from a A/PR/8/34 virus (typically 6 segments from A/PR/8/34, with the HA and NA segments being from a vaccine strain, i.e. a 6:2 reassortant). It may also include one or more RNA segments from a A/WSN/33 virus, or from any other virus strain useful for generating reassortant viruses for vaccine preparation. A reassortant influenza A virus may include fewer than 6 (i.e. 1, 2, 3, 4 or 5) viral segments from an AA/6/60 influenza virus (A/Ann Arbor/6/60). A reassortant influenza B virus may include fewer than 6 (i.e. 1, 2, 3, 4 or 5) viral segments from an AA/1/66 influenza virus (B/Ann Arbor/1/66).

The reassortant influenza strain of the invention may comprise one or more genome segments from an A/California/4/09 strain, preferably the HA segment and/or the NA segment as these are the main vaccine antigens. Thus, for instance, the HA gene segment may encode a H1 hemagglutinin which is more closely related to SEQ ID NO: 7 than to SEQ ID NO: 8 (i.e. has a higher degree sequence identity when compared to SEQ ID NO: 7 than to SEQ ID NO: 8 using the same algorithm and parameters). SEQ ID NOs: 7 and 8 are 80% identical. Similarly, the NA gene may encode a N1 neuraminidase which is more closely related to SEQ ID NO: 9 than to SEQ ID NO: 10. SEQ ID NOs: 9 and 10 are 82% identical.

Reassortant influenza B virus can also be produced. Influenza B viruses do not currently display different HA subtypes, but they do fall into two distinct lineages: B/Victoria/2/87-like and B/Yamagata/16/88-like. These lineages emerged in the late 1980s and have HAs which can be antigenically and/or genetically distinguished from each other [1]. A reassortant influenza B strain of the invention can comprise HA from a B/Victoria/2/87-like strain or a B/Yamagata/16/88-like strain.

Viral segments and sequences from the A/PR/8/34, A/AA/6/60, B/AA/1/66, and A/California/04/09 strains are widely available. Their sequences are available on the public databases e.g. GI:89779337, GI:89779334, GI:89779332, GI:89779320, GI:89779327, GI:89779325, GI:89779322, GI:89779329, see also SEQ ID NOs 1-6.

The choice of backbone strain can depend on the vaccine strain with which it is used. In general, it will be desirable to choose strains whose HA and/or NA segments do not show a high degree of identity on the nucleic acid or amino acid level as this can make it easier to find inhibitory agents which preferentially reduce transcription and/or translation of the backbone strain's HA and/or NA segments. For example the degree of identity may be less than 99%, less than 95%, less than 90%, less than 85%, less than 80% or less than 75%. The HA and/or NA viral segments of the backbone and the vaccine strain can be of different subtypes. For example, when a H3N2 strain is used as a vaccine strain a backbone strain which has a H1N1 subtype (e.g. A/PR/8/34) can be used or vice versa. It is also possible, however, to use a backbone strain and a vaccine strain with the same HA and/or NA subtypes (e.g. a H1 vaccine strain and a H1 backbone strain) in the methods of the invention provided that the transcription and/or translation of the backbone strain's HA and/or NA genes can be preferentially reduced.

Inhibitory Agents

Suitable inhibitory agents for use in the invention are those which can preferentially reduce the transcription and/or translation of the backbone strain's HA and/or NA gene(s) relative to the vaccine strain's HA and/or NA gene(s). The preferential reduction of the backbone strain's HA and/or NA protein levels either at the transcriptional or translational level favours the formation of reassortant influenza viruses because the likelihood increases that the HA and/or NA proteins of the vaccine strain will be incorporated as their relative abundance increases.

Where the inhibitory agent is a transcriptional inhibitor, it will be considered to preferentially reduce transcription if it reduces transcription of the backbone strain's HA and/or NA gene(s) by at least x+5% (e.g. x+10%, x+20%, x+30%, x+40%) provided that the inhibitory agent reduces transcription of the vaccine strain's HA and/or NA genes by x % or less (e.g. x−5%, x−10%, x−20%, x−30% or x−40%), wherein the reduction is measured in comparison to a control sample which was not treated with the inhibitory agent. In this context, x can be 0, 5, 10, 15, 20, 25, 30, 35, 40, 45, 50, 55, 60, 65, 70, 75, 80, 85, 90, 95 or 99. Thus, for example, where the transcription of the backbone strain's HA gene is reduced by 30%, the transcription of the vaccine strain's HA should be reduced by a maximum of 25%. Suitable methods for measuring the transcriptional reduction of the genes by the inhibitory agent will be evident to the skilled person. For example, two separate cell cultures can be infected with the influenza virus of interest. One of the infected cultures is contacted with the inhibitory agent of interest while the other infected culture is either not treated or treated with a substance which is known not to reduce transcription of the HA and/or NA gene(s) of the influenza virus with which the culture was infected (for example, phosphate buffer saline (PBS) or an inhibitory agent with specificity for an unrelated gene). RNA can then be isolated from both samples, cDNA can be transcribed from the isolated RNA and real-time PCR can be performed with the cDNA from both samples using primers specific for the HA and/or NA gene(s) in order to compare the expression levels of the genes in the presence and absence of the inhibitory agent.

A translational inhibitor will be considered to preferentially reduce translation of the backbone strain's HA and/or NA gene(s) if it reduces the backbone strain's HA and/or NA protein levels by at least y+5% (e.g. x+10%, x+20%, x+30%, x+40%) provided that the inhibitory agent reduces translation of the vaccine strain's HA and/or NA genes by y % or less (e.g. x−5%, x−10%, x−20%, x−30% or x−40%), wherein the reduction is measured in comparison to a control sample which was not treated with the inhibitory agent. In this context, y can be 0, 5, 10, 15, 20, 25, 30, 35, 40, 45, 50, 55, 60, 65, 70, 75, 80, 85, 90, 95 or 99. Thus, for example, where the translation of the backbone strain's HA gene is reduced by 30%, the transcription of the vaccine strain's HA should be reduced by a maximum of 25%. Suitable methods for measuring reduction of translation of the HA and/or NA genes will be evident to the skilled person. For example, two separate cell cultures can be infected with the influenza virus. One of the infected cultures is contacted with the inhibitory agent of interest while the other infected culture is either not treated or treated with a substance which is known not to inhibit translation of the HA and/or NA protein(s) of the influenza virus with which the culture was infected (for example, PBS or an inhibitory agent with specificity for an unrelated gene). Proteins can be isolated from both samples and the protein levels of the HA and/or NA protein(s) can be analysed and compared by quantitative western blot analysis (see, for example, chapter 57 of reference 2).

Where more than one backbone strain is used in the methods of the invention, an inhibitory agent will be suitable if it preferentially reduces the transcription and/or translation of the HA and/or NA genes of at least one of the backbone strains used.

It is not generally necessary to test the suitability of the inhibitory agent(s) each time an influenza virus is reassorted in accordance with the present invention as a backbone strain used for reassortment can be used for a variety of different vaccine strains. Thus, once a suitable inhibitory agent(s) for a particular backbone strain has been identified, it is possible to use the same agent(s) for all methods where that particular backbone strain is used, and it is necessary only to verify that the inhibitory agent preferentially reduces transcription and/or translation of the backbone strain's HA and/or NA genes relative to the HA and/or NA genes of the vaccine strain which is used.

Suitable inhibitory agents will be known to the skilled person and include, but are not limited to, short interfering RNAs (siRNA), double-stranded RNAs (dsRNA), micro-RNAs (miRNAs), short hairpin RNAs (shRNA), or small interfering DNAs (siDNAs) like e.g., phosphorothioate oligomers (PSOs) or phosphorodiamidate morpholino oligomer (PMOs).

Short interfering RNAs (siRNAs) are particularly suitable for use in the methods of the present invention. This is because they can be synthesized quickly and cheaply and they can suppress expression of a gene with high specificity. Even a difference of a single nucleotide between the target sequence and an off-target sequence can achieve specific silencing of the target sequence [3]. The use of siRNAs in eggs has, for example, been described in reference 4.

Methods for designing siRNAs that specifically silence a gene of interest are known to those skilled in the art. For example, various programs are available that permit the design of gene specific siRNAs [5, 6]. Examples of such siRNAs for use in the invention are shown in Table 1. The siRNA sequences HA1-HA24 and NA1-NA24 in Table 1 have been designed to differentially inhibit the HA and NA of A/PR/8/34 in the presence of A/Perth/16/09.

The use of siDNAs in the methods of the invention is also preferred. These have the advantage that they are easier to synthesize, are more stable, are taken up more easily by the cell and act faster than siRNAs while still showing a comparable specificity for the target sequence [7].

The use of siRNAs and siDNAs is specifically advantageous when the backbone strain and the vaccine strain have a high degree of identity in their viral segments that encode the HA and/or NA genes, e.g. when they are from the same influenza virus subtype, as these inhibitors are known to show high sequence specificity. In order to achieve preferential reduction of the backbone strain's HA and/or NA protein levels compared to the vaccine strain's HA and/or NA protein levels, the siRNAs and/or siDNAs can be designed such that they target areas of sequence variations between the HA and/or NA genes from the backbone strain and the vaccine strain. Areas of sequence variation can be determined by aligning the sequences from the two strains.

Specific examples of siDNAs are PMOs. These are synthetic antisense oligomers which are usually designed to bind to the translation start site where they can interfere with progression of the ribosomal initiation complex from the 5' cap to the start codon. The advantage of PMOs is that they are more stable compared to RNA or even DNA [8]. Methods for designing PMOs are known in the art [9].

Other suitable inhibitory agents are PSOs. These are synthetic oligomers wherein an oxygen atom is replaced by a non-bridging sulfur in the oligophosphate backbone of the DNA. PSOs are advantageous as they are more stable compared to unmodified DNA and RNA oligomers.

When shRNAs are used they are usually introduced into the culture host as a DNA expression construct that can express the shRNA. These shRNA expression constructs will typically contain a sequence encoding a siRNA molecule and the reversed complementary sequence of the siRNA molecule separated by a short linker sequence on the same DNA strand. The siRNA sequence can be designed as described above and it is within the means of the skilled person to identify the reverse complementary sequence once the siRNA sequence is known. Examples of DNA sequences that encode suitable shRNAs for use in the invention are shown in Table 2. The sequences in this table use 'GGGGGGG' as an exemplary linker sequence but the skilled person can easily replace it with other suitable sequences.

It is also envisioned to use more than one kind of inhibitory agent in the methods of the present invention.

The use of further inhibitory agents in addition to or instead of those with specificity for the HA and/or NA gene(s) of the backbone strain is also within the scope of the present invention. For example, it is possible to add one or more inhibitory agents which can preferentially reduce the transcription and/or translation of one or more of the vaccine strain's backbone segments. This has the advantage that the likelihood of formation of desired reassortant viruses is further increased. Suitable inhibitory agents can be identified by the same means mutatis mutandis as described above for inhibitory agents that preferentially reduce transcription and/or translation of the backbone strain's HA and/or NA genes.

The inhibitory agent can be introduced into the individual cells in the cell culture or the egg (allantoic fluid) by any means known to those of skill in the art. For example, they can be introduced by electroporation, DEAE-dextran, calcium phosphate precipitation, liposomes, microinjection, or microparticle-bombardment.

Where the reassortant viruses are produced in cell culture, it is possible to use cells which have been stably transfected with one or more expression constructs encoding the inhibitory agent(s). This has the advantage that the same cell line can be used each time a particular backbone strain is employed thus eliminating the need to separately introduce inhibitory agent(s) each time the methods of the invention are practised.

The one or more inhibitory agent(s) can be introduced into the host cell or the allantoic fluid before, during or after infection with the influenza virus(es).

Virus Reassortment

Reassortant influenza viruses are frequently produced by co-infecting a culture host, usually cell culture or eggs, with a backbone strain and a vaccine strain. Reassortant viruses are selected by adding antibodies with specificity for the HA and/or NA proteins of the backbone strain in order to select for reassortant viruses that contain the vaccine strain's HA and/or NA proteins. Over several passages of this treatment one can select for fast-growing reassortant viruses containing the vaccine strain's HA and/or NA segments.

Reassortant influenza viruses between two, three or more different influenza strains can be produced. The reassortant viruses produced contain at least one (i.e. one, two, three, four, five or six) backbone viral segment from the backbone strain. The backbone viral segments are those which do not encode HA or NA. Thus, backbone segments will typically encode the PB1, PB2, PA, NP, $M_1$, $M_2$, $NS_1$ and $NS_2$ polypeptides of the influenza virus. The reassortant viruses will not typically contain the segments encoding HA and NA from the backbone strain even though reassortant viruses which comprise either the HA or the NA but not both from the backbone strain are also envisioned.

When the reassortant viruses are reassortants between two influenza strains, the reassortant viruses will generally include segments from the backbone strain and the vaccine strain in a ratio of 1:7, 2:6, 3:5, 4:4, 5:3, 6:2 or 7:1. Having a majority of segments from the backbone strain, in particular a ratio of 6:2, is typical. When the reassortant viruses of the invention are reassortants of three strains, the reassortant virus will generally include segments from the backbone strain, the vaccine strain and the third strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1 or 6:1:1. For example, the reassortant influenza strains may contain viral segments from more than one backbone strain and/or more than one vaccine strain.

The 'second influenza strain' used in the methods of the invention is different to the first influenza strain which means that one or more (e.g. 2, 3, 4, 5, 6, 7, or 8) of their viral segments will be different.

Reverse Genetics

The invention will usually be applied in the context of "traditional" reassortment techniques, but it can also be used in reverse genetics (RG) systems or in combinations of traditional reassortment techniques and RG systems. A problem with some RG systems is that it can be hard to introduce the required expression constructs into a culture host (due to low transfection efficiency, for example) which can make the RG system inefficient. The invention overcomes this problem by providing a method wherein some of the viral segments for the reassortant influenza virus are provided by infecting the culture host with an influenza virus while others are provided on one or more expression constructs.

In the methods of the invention, a culture host is infected with a first influenza A or B strain which has eight genome segments of which at least one (for example, one, two, three, four, five, or six) are target segments. The target segment(s) from the first influenza strain are those viral segments which will not be present in the reassortant influenza virus produced according to the methods of the invention. The target segments of a second influenza virus strain are introduced on one or more expression construct(s). The target segment(s) of the second influenza strain are those segment(s) which will be present in the reassortant influenza virus produced according to the methods of the invention. The transcription and/or translation of the first influenza strain's target segment(s) is preferentially reduced by the inhibitory agent. Typically, the first influenza strain will have one or two target segments (usually HA and/or NA) and accordingly one or two target segments from the second influenza strain are introduced on one or more expression construct(s). The inhibitory agent(s) may be encoded on the same construct as the second influenza strain's segment(s) or on different construct(s).

For example, when the vaccine strain's HA segment is introduced into the culture host on an expression construct and the culture host is infected with the backbone strain, the inhibitory agent will be specific for the backbone strain's HA segment. Similarly, when the vaccine strain's NA is introduced on the one or more expression construct(s), the inhibitory agent will be specific for the backbone strain's NA segment. If both the HA and NA segments are introduced on the one or more expression construct(s), the inhibitory agent will be specific for the backbone strain's HA and NA segments. The target segment(s) will typically be HA and/or NA.

The viral segments introduced on the one or more expression construct(s) can be the HA and/or NA segments of the vaccine strain while the backbone segments are provided by the influenza virus used to infect the culture host. In this embodiment, the culture host can be contacted with inhibitory agents which preferentially reduce transcription and/or translation of the backbone strain's HA and/or NA segments. It is also possible to provide one or more backbone segment(s) on the expression construct(s).

The first and the second influenza virus are different. Furthermore, in the methods of the invention, the steps of (i) infecting the culture host with a virus, (ii) introducing the one or more expression construct(s) into the culture host and (iii) contacting the culture host with an inhibitory agent can be performed in any order.

Furthermore, although most RG systems permit ready omission of a backbone strain's segments, in other systems this is not so easy. For example, some RG systems encode 6 viral segments on a first plasmid plus the HA and NA genes on a second plasmid. It can thus be cumbersome to create a reassortant strain in which one of the first plasmid's segments is replaced, but the present invention overcomes this issue. For example, a RG system encoding a first strain can be modified to encode a segment from a second strain and also to inhibit the corresponding segment for the first strain, thereby providing a reassortant in which this segment for the second strain replaces the first strain's. Thus the invention provides a cell comprising expression construct(s) encoding: (i) all eight genome segments of a first influenza A or B virus genome; (ii) at least one target segment of a second influenza A or B virus genome, wherein the second influenza strain's target segment(s) differ(s) in sequence from the target segment(s) of the first influenza strain; and (iii) an inhibitory agent wherein said inhibitory agent preferentially reduces transcription and/or translation of the target segment(s) in the first influenza strain.

The target segment will typically include HA and/or NA. For example, the cell may comprise expression construct(s) encoding: (i) all eight segments of a backbone strain; (ii) at least a HA segment of a vaccine strain influenza, wherein the vaccine strain's HA segment differs in sequence from the backbone strain's HA segment; and (iii) an inhibitory agent wherein said inhibitory agent preferentially reduces transcription and/or translation of the backbone strain's HA segment.

The cell can produce influenza virus containing a reassortant mixture of backbone and vaccine strain segments. Virus produced by the cell can be used for vaccine manufacture as described herein.

The backbone strain's segments will typically be encoded on a different expression construct from the vaccine strain's segment(s). The inhibitory agent(s) may be encoded on the same construct as the vaccine strain's segment(s) or on different construct(s). For example, a first construct may encode all eight segments of an influenza virus. A second construct can be added which encodes a vaccine strain's HA and NA segments and which also encodes inhibitors of the backbone strain's HA and NA segments.

Viral RNA (vRNA) molecules can be expressed in a construct under the control of, for example, pol I promoters, bacterial RNA polymerase promoters, bacteriophage polymerase promoters, etc. Where certain proteins are required to form an infectious virus the RG system can provide these proteins e.g. the system further comprises DNA molecules that encode viral proteins such that expression of both types of DNA leads to assembly of a complete infectious virus.

Culture Host

The culture host for use in the methods of the present invention can be embryonated hen eggs or cells.

The current standard method for influenza virus growth uses specific pathogen-free (SPF) embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoic fluid of the egg together with the virus [10].

When cells are used, the invention will typically use a cell line although, for example, primary cells may be used as an alternative. The cell will typically be mammalian. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [11-13]. Suitable dog cells are e.g. kidney cells, as in the CLDK and MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [14-17], derived from Madin Darby canine kidney; Vero cells [18-20], derived from African green monkey (*Cercopithecus aethiops*) kidney; or PER.C6 cells [21], derived from human embryonic retinoblasts. These cell lines are widely available e.g. from the American Type Cell Culture (ATCC) collection [22], from the Coriell Cell Repositories [23], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 24-26], including cell lines derived from ducks (e.g. duck retina) or hens e.g. chicken embryo fibroblasts (CEF), etc. Examples include avian embryonic stem cells [24,27], including the EBx cell line derived from chicken embryonic stem cells, EB45, EB14, and EB14-074 [28].

Preferred cells for use in the invention are MDCK cells [29-31], derived from Madin Darby canine kidney. The original MDCK cells are available from the ATCC as CCL-34. Derivatives of MDCK cells may also be used. For instance, reference 14 discloses a MDCK cell line that was adapted for growth in suspension culture ('MDCK 33016', deposited as DSM ACC 2219). Similarly, reference 32 discloses a MDCK-derived cell line that grows in suspension in serum-free culture ('B-702', deposited as FERM BP-7449). Reference 33 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 34 discloses MDCK cell lines with high susceptibility to infection, including 'MDCK.5F1' cells (ATCC CRL-12042). Any of these MDCK cell lines can be used.

For growth on a cell line, such as on MDCK cells, virus may be grown on cells in suspension [14,35,36] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention if it contains no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [37] (e.g. 30-36° C., or at about 30° C., 31° C., 32° C., 33° C., 34° C., 35° C., 36° C.), for example during viral replication.

Where virus is grown on a cell line then the growth culture, and also the viral inoculum used to start the culture, is preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [38].

Where virus has been grown on a mammalian cell line then the composition will advantageously be free from egg proteins (e.g. ovalbumin and ovomucoid) and from chicken DNA, thereby reducing allergenicity. The avoidance of allergens is useful for minimizing Th2 responses.

Virus Preparation

In a further aspect, the invention provides a method for the preparation of an influenza virus.

Where cells are used as a culture host in the methods of the invention, it is known that cell culture conditions (e.g. temperature, cell density, pH value, etc.) are variable over a wide range subject to the cell line and the influenza virus strain employed and can be adapted to the requirements of the application. The following information therefore merely represents guidelines.

Cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. After infection with the influenza viruses, the cells are preferably cultured at a temperature of between 30° C. and 36° C. or between 32° C. and 34° C. or at about 33° C. This is particularly preferred as it has been shown that incubation of infected cells in this temperature range results in production of a virus that results in improved efficacy when formulated into a vaccine [39].

The oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8-25\times10^5$ cells/mL in the batch system or preferably about $5-20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. The cells may also be adapted for growth in suspension.

The methods according to the invention can include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is preferred that the viruses are inactivated during or after purification. Virus inactivation can occur, for example, by β-propiolactone or formaldehyde at any point within the purification process.

Vaccine

The invention utilises virus produced according to the method to produce vaccines.

Influenza vaccines are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated influenza virus is used, the vaccine may comprise whole virion, split virion, or purified surface antigens (including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution (that optionally includes detergent to disrupt the virions) or affinity chromatography methods. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 40-45, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethylene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [46] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The method of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 47). Live virus vaccines include MedImmune's FLUMIST™ product (trivalent live virus vaccine).

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [48,49]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the compositions of the invention are particularly useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [50] and/or zanamivir), including resistant pandemic strains [51].

Compositions of the invention may include antigen(s) from one or more (e.g. 1, 2, 3, 4 or more) influenza virus strains, including influenza. A virus and/or influenza. B virus. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [52], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s) (a thorough discussion of such components is available in reference 53). As described below, adjuvants may also be included.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 µg/ml) mercurial material e.g. thiomersal-free [44, 54]. Vaccines containing no mercury are more preferred. An α-tocopherol succinate can be included as an alternative to mercurial compounds [44]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [55], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 56 & 57, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [58].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 µm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EU), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcho line (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANS), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [59].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [60-62], as described in more detail in Chapter 10 of ref. 63 and chapter 12 of ref. 64. The MF59 emulsion advantageously includes citrate ions e.g. 10 mM sodium citrate buffer.

An emulsion of squalene, DL-α-tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene: tocopherol is preferably ≤1 as this provides a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [65].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalene, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [66] (0.05-1% Thr-MDP, 5% squalane, 2.5% Pluronic L121 and 0.2% polysorbate 80). It can also be used without the Thr-MDP, as in the "AF" adjuvant [67] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [68]. The emulsion may also include one or more of: alditol; a cryoprotective agent (e.g. a sugar, such as dodecylmaltoside and/or sucrose); and/or an alkylpolyglycoside. The emulsion may include a TLR4 agonist [69]. Such emulsions may be lyophilized.

An emulsion of squalene, poloxamer 105 and Abil-Care [70]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 71, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 72, produced by addition of aliphatic amine to desacylsaponin via the carboxyl group of glucuronic acid), dimethyldioctadecylammonium bromide and/or N,N-dioctadecyl-N, N-bis(2-hydroxyethyl)propanediamine.

An emulsion in which a saponin (e.g. QuilA or QS21) and a sterol (e.g. a cholesterol) are associated as helical micelles [73].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [74].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [74].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and 5/8-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [75]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [76-78], oral [79], intradermal [80,81], transcutaneous, transdermal [82], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 83. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 84.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 83. A preferred alignment program is GCG Gap (Genetics Computer Group, Wisconsin, Suite Version 10.1), preferably using default parameters, which are as follows: open gap=3; extend gap=1.

BRIEF DESCRIPTION OF THE DRAWINGS

FIGS. 1 and 2 show the viral titer after incubating with the indicated siRNAs. FIG. 1 shows the viral titer of A/PR8/34 and FIG. 2 shows the viral titer of A/Victoria (H3N2).

MODES FOR CARRYING OUT THE INVENTION

Example 1

A reassortant influenza virus is produced using the A/PR/8/34 influenza strain as a backbone strain and the A/Brisbane/10/07-like or A/Perth/16/09-like influenza strain as vaccine strain. Inhibitory agents (e.g. siRNAs, PSOs or PMOs) are designed such that they preferentially reduce transcription and/or translation of the HA and/or NA gene(s) of the A/PR/8/34 strain.

The suitability of the inhibitory agents is tested by introducing the inhibitory agent into a culture host and subsequently co-infecting the culture host with the backbone strain and the vaccine strain. Protein is extracted from the infected cells and the preferential reduction of the backbone strain's HA and/or NA protein levels is assessed by comparing the protein levels of the vaccine strain's and the backbone strain's HA and/or NA proteins by quantitative Western blot analysis.

Reassortant influenza viruses are produced by introducing the inhibitory agent into the culture host and infecting the culture host with the backbone and the vaccine strain. The culture host is cultured under conditions suitable for producing the reassortant influenza virus.

Example 2

Inhibitory agents of the invention were selected by comparing their effects on the growth of the backbone strain to their effects on the growth of the vaccine strain.

The following virus strains were tested:
A/PR/8/34 (the backbone strain); and
A/Victoria (H3N2) (the vaccine strain).

Although they were designed for inhibiting A/PR/8/34 in the presence of A/Perth/16/09, the following siRNAs were tested:

HA2, HA7-HA12 and HA19 from Table 1 (targeting HA); and

NA4, NA6-NA9, NA11, NA12 and NA22 from Table 1 (targeting NA).

Experimental controls include no treatment (no TF no siRNA), transfection only (i.e. no siRNA; TF no siRNA) and control siRNAs (K1, K2) that do not target the virus.

The siRNAs were introduced into MDCK cells in parallel experiments. The MDCK cells were subsequently infected with the virus, and the viral titer was measured.

The results are shown in FIGS. 1 and 2. All tested siRNAs targeting HA show reduction of A/PR/8/34 growth. siRNAs NA4, NA6, NA7, NA12 and NA22 show reduction of A/PR/8/34 growth. siRNAs HA7, HA8, HA10, NA7, NA9, NA11 and NA12 do not significantly inhibit A/Victoria growth. Suitable inhibitory agents of the invention would block backbone strain replication but allow propagation of the vaccine strain. Therefore, siRNAs HA7, HA8, HA10, NA7 and NA9 are suitable inhibitory agents of the invention when using A/PR/8/34 and A/Victoria.

It will be understood that the invention has been described by way of example only and modifications may be made whilst remaining within the scope and spirit of the invention.

TABLE 1

| Strain | siRNA sequences (antisense strand) | | |
|---|---|---|---|
| *A/Puerto Rico/8/34* | | | |
| HA | GGGCCUCUGUGUUAUUAUA | SEQ ID NO: | 49 |
| | UGGGCCUCUGUGUUAUUAU | SEQ ID NO: | 11 |
| | UGAGACUCUUACCUUAUAC | SEQ ID NO: | 12 |
| | GGGCCUCUGUGUUAUUAUA | SEQ ID NO: | 13 |
| | GACCCUCCUACUUGAUAAU | SEQ ID NO: | 14 |
| | GGGCCUUUAUCGUCUUUCU | SEQ ID NO: | 15 |
| | CCGUUUACCUUUAGAUUAU | SEQ ID NO: | 16 |
| | CAGAGGGAAAGGUCUUAUA | SEQ ID NO: | 17 |
| | CCCUCCUACUUGAUAAUGA | SEQ ID NO: | 18 |
| | CAGGAUGUAACAUCUUUGU | SEQ ID NO: | 19 |
| | CUGGGUUUCAUUCUCUAGU | SEQ ID NO: | 20 |
| NA | CCUGAUUAAUCGGAUUAUA | SEQ ID NO: | 21 |
| | CCCGAUAUAUGUCGUUUCU | SEQ ID NO: | 22 |
| | CGAAGACCCAACUUAAUUA | SEQ ID NO: | 23 |
| | GCCUGAUUAAUCGGAUUAU | SEQ ID NO: | 24 |
| | CGGACACAUUUACCAAGUA | SEQ ID NO: | 25 |
| | CGGGAAAUAAAGUACAAGA | SEQ ID NO: | 26 |
| | GCCGUUAAGUAGAGAAACA | SEQ ID NO: | 27 |
| | CGCCUUCAAAGCAAGUUGU | SEQ ID NO: | 28 |
| | CAGACCAUCAGCCUGAUUA | SEQ ID NO: | 29 |
| | CCCUGACAAUUCCUGUCUU | SEQ ID NO: | 30 |
| | CACCCGAUAUAUGUCGUUU | SEQ ID NO: | 31 |
| *A/Ann Arbor/6/60* | | | |
| HA | GUAAAGCUCUUUCAUUUCU | SEQ ID NO: | 32 |
| | CGCCUCUUGUUUACGAUUA | SEQ ID NO: | 33 |
| | CCUCUUGUUUACGAUUAUU | SEQ ID NO: | 34 |
| | CUCGUUAUUUAUGUUGUA | SEQ ID NO: | 35 |
| | CACGGUCUUACCAGGAUAU | SEQ ID NO: | 36 |
| | GCCUCUUGUUUACGAUUAU | SEQ ID NO: | 37 |
| | GUCCGUUGAAGUUACUAAU | SEQ ID NO: | 38 |
| | CGUGGUCUCAUACCUAAGU | SEQ ID NO: | 39 |
| | GGUCUUACCAGGAUAUAUU | SEQ ID NO: | 40 |
| NA | CCGGGCAAUAUCUGUAUUU | SEQ ID NO: | 41 |
| | CGGGCAAUAUCUGUAUUUA | SEQ ID NO: | 42 |
| | CCCACAAGGUAAAGUAAAU | SEQ ID NO: | 43 |
| | CCCGCUUGUAGUUAAAGUA | SEQ ID NO: | 44 |
| | CGGCGUUACAGUUUAAUGU | SEQ ID NO: | 45 |
| | GGGAGUAGCUUGGGAUAUU | SEQ ID NO: | 46 |
| | CGGCUAUGAUCUUAUGAUA | SEQ ID NO: | 47 |
| | CCUGGAGUUUGUCAUAACA | SEQ ID NO: | 48 |
| | CGGUACACUUGGUUAUUAU | SEQ ID NO: | 50 |

TABLE 1-continued

| Strain | siRNA sequences (antisense strand) | | |
|---|---|---|---|
| *A/Chile/1/83* | | | |
| HA | CUGGUCUUAAAGUCUUUAU | SEQ ID NO: | 51 |
| | CCGUUUACCUUUAGAUUAU | SEQ ID NO: | 52 |
| | GGACCUGUAAACCUGUAUA | SEQ ID NO: | 53 |
| | CCCUGUGUUAUUAUAAACU | SEQ ID NO: | 54 |
| | CUGGGUUUCAUUCUUUAGU | SEQ ID NO: | 55 |
| | GACCUGUAAACCUGUAUAU | SEQ ID NO: | 56 |
| | CUCCUUGACUCCCUUGUUA | SEQ ID NO: | 57 |
| | CCCAUUUCUUAAGUUGUUU | SEQ ID NO: | 58 |
| | CCAGAAACGUCACGUCUUA | SEQ ID NO: | 59 |
| | CAGGAUGUAACGUCUUUGU | SEQ ID NO: | 60 |
| NA | CUGGGUUCCACGAGAUAAU | SEQ ID NO: | 61 |
| | CCCGAUAUAUGUCGUUUCU | SEQ ID NO: | 62 |
| | CGAAGACCCAACUUAAUUA | SEQ ID NO: | 63 |
| | GACCCAUUUAGUUUGUAUA | SEQ ID NO: | 64 |
| | GCCGUUAAGUAGAGAAACA | SEQ ID NO: | 65 |
| | CGAGGUCUUUCCCUAAACU | SEQ ID NO: | 66 |
| | GGUUCCACGAGAUAAUUUA | SEQ ID NO: | 67 |
| | CGCCUUCAAAGCAAGUUGU | SEQ ID NO: | 68 |
| | CCCAUUUAGUUUGUAUACA | SEQ ID NO: | 69 |
| | CGGAGCAUGUCUUAGAAGU | SEQ ID NO: | 70 | siRNAs that differentially inhibit PR/8/34 relative to A/Perth/16/09*

| | | | | |
|---|---|---|---|---|
| HA | TTTGGGATAATCATAAGTC | SEQ ID NO: | 71 | HA1 |
| | TTTGTTGAATTCTTTACCC | SEQ ID NO: | 72 | HA2 |
| | TTCTGCACTGCAAAGATCC | SEQ ID NO: | 73 | HA3 |
| | TTGATTCCAATTTCACTCC | SEQ ID NO: | 74 | HA4 |
| | TTCTTTGGGAAATATTTCG | SEQ ID NO: | 75 | HA5 |
| | TAATCTCAGATGCATATTC | SEQ ID NO: | 76 | HA6 |
| | TTCATTCTCATACAGATTC | SEQ ID NO: | 77 | HA7 |
| | TTCACCTTGTTTGTAATCC | SEQ ID NO: | 78 | HA8 |
| | TTTCTTACACTTTCCATGC | SEQ ID NO: | 79 | HA9 |
| | TAGACCTCTGGATTGAATG | SEQ ID NO: | 80 | HA10 |
| | TACTTTCTCATACAGATTC | SEQ ID NO: | 81 | HA11 |
| | TACACTCATGCATTGATGC | SEQ ID NO: | 82 | HA12 |
| | TTTGGTGTTTCTACAATGT | SEQ ID NO: | 83 | HA13 |
| | TCAGCTTTGGGTATGAGCC | SEQ ID NO: | 84 | HA14 |
| | TAGTCCTGTAACCATCCTC | SEQ ID NO: | 85 | HA15 |
| | ATTTCTTACACTTTCCATG | SEQ ID NO: | 86 | HA16 |
| | TACTGTGTCAACAGTGTCG | SEQ ID NO: | 87 | HA17 |
| | TTACACTTTCCATGCATTC | SEQ ID NO: | 88 | HA18 |
| | TTTGTAATCCCGTTAATGG | SEQ ID NO: | 89 | HA19 |
| | ATAGAGATTCTGTTGTTCC | SEQ ID NO: | 90 | HA20 |
| | TTGGGATAATCATAAGTCC | SEQ ID NO: | 91 | HA21 |
| | TTGAATTCTTTACCCACAG | SEQ ID NO: | 92 | HA22 |
| | TTTGTGTTGTGGTTGGGCC | SEQ ID NO: | 93 | HA23 |
| | TTCTTCTCGAGTACTGTGT | SEQ ID NO: | 94 | HA24 |
| NA | TACAGTATCACTATTCACG | SEQ ID NO: | 95 | NA1 |
| | TTTAATACAGCCACTGCTC | SEQ ID NO: | 96 | NA2 |
| | ATTGATTTAGTAACCTTCC | SEQ ID NO: | 97 | NA3 |
| | TATCTGGACCTGAAATTCC | SEQ ID NO: | 98 | NA4 |
| | TTGATTTAGTAACCTTCCC | SEQ ID NO: | 99 | NA5 |
| | TTGAATTGAATGCTAATC | SEQ ID NO: | 100 | NA6 |
| | TTGCTGTATATAGCCCACC | SEQ ID NO: | 101 | NA7 |
| | TTGCCGGTTAATATCACTG | SEQ ID NO: | 102 | NA8 |
| | TAACAGTCCCACTTGAATG | SEQ ID NO: | 103 | NA9 |
| | TTTGGTTGCATATTCCAGT | SEQ ID NO: | 104 | NA10 |
| | TATTAGGCTAATTAGTCCG | SEQ ID NO: | 105 | NA11 |
| | TTTGGAACCAATTCTTATG | SEQ ID NO: | 106 | NA12 |
| | ATCTACAGTATCACTATTC | SEQ ID NO: | 107 | NA13 |
| | TACTTGTCAATGCTGAATG | SEQ ID NO: | 108 | NA14 |
| | TTACTATCAGTCTCTGTCC | SEQ ID NO: | 109 | NA15 |
| | TTGACTTCCAGTTTGAATT | SEQ ID NO: | 110 | NA16 |
| | ATTAATTCAACCCAGAAGC | SEQ ID NO: | 111 | NA17 |
| | TCCTATTTGATAATCCAGG | SEQ ID NO: | 112 | NA18 |
| | TGAATTGAATGGCTAATCC | SEQ ID NO: | 113 | NA19 |
| | TTCCAGTTTGAATTGAATG | SEQ ID NO: | 114 | NA20 |
| | ATGGTTTCAGTTATTATGC | SEQ ID NO: | 115 | NA21 |
| | ATGTTGAACGAAACTTCCG | SEQ ID NO: | 116 | NA22 |

TABLE 1-continued

| Strain | siRNA sequences (antisense strand) | | |
|---|---|---|---|
| | ATTGCCACAACATCTTGCC | SEQ ID NO: 117 | NA23 |
| | TTGGAACCAATTCTTATGC | SEQ ID NO: 118 | NA24 |

*The following sequences are provided in DNA format and only the antisense strand of each siRNA is shown. For the experiments, the inventors used double stranded RNAs (i.e. G, A, C and U ribonucleotides) based on the sequences below, and both siRNA strands contained 2 additional U nucleotides as overhangs at the 3'ends.

TABLE 2

| Strain | Sequences |
|---|---|
| HA | |
| A/Puerto Rico/8/34 | GGGCCTCTGTGTTATTATAGGGGGGGTATAATAACACAGAGGCCC (SEQ ID NO: 119) |
| | TGGGCCTCTGTGTTATTATGGGGGGGATAATAACACAGAGGCCCA (SEQ ID NO: 120) |
| A/Ann Arbor/6/60 | GTAAAGCTCTTTCATTTCTGGGGGGGAGAAATGAAAGAGCTTTAC (SEQ ID NO: 121) |
| | CGCCTCTTGTTTACGATTAGGGGGGGTAATCGTAAACAAGAGGCG (SEQ ID NO: 122) |
| A/Chile/1/83 | CTGGTCTTAAAGTCTTTATGGGGGGGATAAAGACTTTAAGACCAG (SEQ ID NO: 123) |
| | CCGTTTACCTTTAGATTATGGGGGGGATAATCTAAAGGTAAACGG (SEQ ID NO: 124) |
| NA | |
| A/Puerto Rico/8/34 | CCTGATTAATCGGATTATAGGGGGGGTATAATCCGATTAATCAGG (SEQ ID NO: 125) |
| | CCCGATATATGTCGTTTCTGGGGGGGAGAAACGACATATATCGGG (SEQ ID NO: 126) |
| A/Ann Arbor/6/60 | CCGGGCAATATCTGTATTTGGGGGGGAAATACAGATATTGCCCGG (SEQ ID NO: 127) |
| | CGGGCAATATCTGTATTTAGGGGGGGTAAATACAGATATTGCCCG (SEQ ID NO: 128) |
| A/Chile/1/83 | CTGGGTTCCACGAGATAATGGGGGGGATTATCTCGTGGAACCCAG (SEQ ID NO: 129) |
| | CCCGATATATGTCGTTTCTGGGGGGGAGAAACGACATATATCGGG (SEQ ID NO: 130) |

REFERENCES

[1] Rota et al. (1992) *J Gen Virol* 73:2737-42.
[2] The Protein Protocols Handbook (ed. Walker). 2nd edition, 2002, ISBN: 0-89603-940-2.
[3] Miller et al. (2003) *PNAS* 100:7195-7200.
[4] Ge et al. (2003) *PNAS* 100:2718-2723.
[5] http://jura.wi.mit.edu/bioc/siRNAext/
[6] http://www.dharmacon.com/designcenter/designcenter-page.aspx
[7] WO2009/030440.
[8] Summerton and Weller (1997) Antisense Nucleic Acid Drug Dev.; 7(3):187-195.
[9] Klee et al. (2005); Nucleic Acids Res. 1; 33.
[10] WO2005/113756.
[11] Kistner et al. (1998) Vaccine 16:960-8.
[12] Kistner et al. (1999) Dev Biol Stand 98:101-110.
[13] Bruhl et al. (2000) Vaccine 19:1149-58.
[14] WO97/37000.
[15] Brands et al. (1999) *Dev Biol Stand* 98:93-100.
[16] Halperin et al. (2002) *Vaccine* 20:1240-7.
[17] Tree et al. (2001) *Vaccine* 19:3444-50.
[18] Kistner et al. (1998) *Vaccine* 16:960-8.
[19] Kistner et al. (1999) *Dev Biol Stand* 98:101-110.
[20] Bruhl et al. (2000) *Vaccine* 19:1149-58.
[21] Pau et al. (2001) *Vaccine* 19:2716-21.
[22] Available at www.atcc.org
[23] Available at locus.umdnj.edu
[24] WO03/076601.
[25] WO2005/042728.
[26] WO03/043415.
[27] WO01/85938.
[28] WO2006/108846.
[29] WO97/37000.
[30] Brands et al. (1999) Dev Biol Stand 98:93-100.
[31] Halperin et al. (2002) Vaccine 20:1240-7.
[32] EP-A-1260581 (WO01/64846).
[33] WO2006/071563.
[34] WO2005/113758.
[35] WO03/023021.
[36] WO03/023025.
[37] WO97/37001.
[38] WO2006/027698.
[39] WO97/37001.
[40] WO02/28422.
[41] WO02/067983.
[42] WO02/074336.
[43] WO01/21151.
[44] WO02/097072.
[45] WO2005/113756.
[46] Huckriede et al. (2003) *Methods Enzymol* 373:74-91.
[47] Vaccines. (eds. Plotkin & Orenstein). 4th edition, 2004, ISBN: 0-7216-9688-0.
[48] Treanor et al. (1996) *J Infect Dis* 173:1467-70.
[49] Keitel et al. (1996) *Clin Diagn Lab Immunol* 3:507-10.
[50] Herlocher et al. (2004) *J Infect Dis* 190(9):1627-30.
[51] Le et al. (2005) *Nature* 437(7062):1108.
[52] WO2008/068631.
[53] Gennaro (2000) *Remington: The Science and Practice of Pharmacy*. 20th edition, ISBN: 0683306472.
[54] Banzhoff (2000) *Immunology Letters* 71:91-96.
[55] Nony et al. (2001) *Vaccine* 27:3645-51.
[56] EP-B-0870508.

[57] U.S. Pat. No. 5,948,410.
[58] WO2007/052163.
[59] WO2007/052061.
[60] WO90/14837.
[61] Podda & Del Giudice (2003) *Expert Rev Vaccines* 2:197-203.
[62] Podda (2001) *Vaccine* 19: 2673-2680.
[63] *Vaccine Design: The Subunit and Adjuvant Approach* (eds. Powell & Newman) Plenum Press 1995 (ISBN 0-306-44867-X).
[64] *Vaccine Adjuvants: Preparation Methods and Research Protocols* (Volume 42 of *Methods in Molecular Medicine* series). ISBN: 1-59259-083-7. Ed. O'Hagan.
[65] WO2008/043774.
[66] Allison & Byars (1992) *Res Immunol* 143:519-25.
[67] Hariharan et al. (1995) *Cancer Res* 55:3486-9.
[68] US-2007/014805.
[69] US-2007/0191314.
[70] Suli et al. (2004) *Vaccine* 22(25-26):3464-9.
[71] WO95/11700.
[72] U.S. Pat. No. 6,080,725.
[73] WO2005/097181.
[74] WO2006/113373.
[75] Potter & Oxford (1979) *Br Med Bull* 35: 69-75.
[76] Greenbaum et al. (2004) *Vaccine* 22:2566-77.
[77] Zurbriggen et al. (2003) *Expert Rev Vaccines* 2:295-304.
[78] Piascik (2003) *J Am Pharm Assoc* (Wash D.C.). 43:728-30.
[79] Mann et al. (2004) *Vaccine* 22:2425-9.
[80] Halperin et al. (1979) *Am J Public Health* 69:1247-50.
[81] Herbert et al. (1979) *J Infect Dis* 140:234-8.
[82] Chen et al. (2003) *Vaccine* 21:2830-6.
[83] *Current Protocols in Molecular Biology* (F. M. Ausubel et al., eds., 1987) Supplement 30.
[84] Smith & Waterman (1981) *Adv. Appl. Math.* 2: 482-489.

The invention claimed is:

1. A culture comprising:
   host cells infected with a first influenza viral strain and a second influenza viral strain,
   wherein the host cells are in contact with a nucleic acid inhibitory agent that preferentially reduces the transcription and/or translation of one or more surface antigens of the first or the second influenza viral strain.

2. The culture of claim 1, wherein the culture is free of animal derived products.

3. The culture of claim 1, wherein the culture is free of added antibodies to the one or more surface antigens.

4. The culture of claim 1, wherein the nucleic acid inhibitory agent is a synthetic antisense oligomer.

5. The culture of claim 1, wherein the nucleic acid inhibitory agent is a phosphorothioate oligomer (PSO).

6. The culture of claim 1, wherein the nucleic acid inhibitory agent is a phosphorodiamidate morpholino oligomer (PMO).

7. The culture of claim 1, wherein the nucleic acid inhibitory agent is selected from the group consisting of:
   short interfering RNAs (siRNA), double-stranded RNAs (dsRl\fA), micro-RNAs (miRNA), short hairpin RNAs (shRNA), and small interfering DNAs (siDNA).

8. The culture of claim 1, wherein the culture is an embryonated hen egg.

9. The culture of claim 1, wherein the host cells are mammalian cells or avian cells.

10. The culture of claim 1, wherein the influenza surface antigens are HA and/or NA.

* * * * *